United States Patent [19]

Davalian et al.

[11] Patent Number: 5,401,649
[45] Date of Patent: Mar. 28, 1995

[54] 2-METHYL-4-HEXENE-AND 3-METHYL-5-HEPTENE-1,2-DIOL DERIVATIVES

[75] Inventors: Dariush Davalian; Cheng-I Lin, both of San Jose; Edwin F. Ullman, Atherton, all of Calif.

[73] Assignee: Syntex (U.S.A.) Inc., Palo Alto, Calif.

[21] Appl. No.: 837,526

[22] Filed: Feb. 18, 1992

Related U.S. Application Data

[62] Division of Ser. No. 93,454, Sep. 4, 1987, Pat. No. 5,089,390.

[51] Int. Cl.$^6$ .................. C12N 9/96; C12N 9/04; A61K 37/00
[52] U.S. Cl. ...................... 435/188; 435/7.9; 435/192; 435/964; 514/11; 530/317; 530/321
[58] Field of Search ............... 435/188, 7.9, 26, 190, 435/962, 964; 514/11; 530/317, 321

[56] References Cited

U.S. PATENT DOCUMENTS

| | | | |
|---|---|---|---|
| 3,875,011 | 4/1975 | Rubenstein | 435/188 |
| 4,096,237 | 6/1978 | Li | 424/1 |
| 4,104,367 | 8/1978 | Gomez et al. | 424/1 |
| 4,117,118 | 9/1978 | Harri et al. | 424/177 |
| 4,123,431 | 10/1978 | Soffer et al. | 260/292 |
| 4,206,199 | 6/1980 | Fujino et al. | 424/85 |
| 4,384,996 | 5/1983 | Bollinger | 260/112.5 |
| 4,396,542 | 8/1983 | Wenger | 260/112.5 R |
| 4,554,351 | 11/1985 | Wenger | 544/177 |
| 4,608,200 | 8/1986 | Khanna et al. | 530/387 |
| 4,608,252 | 8/1986 | Khanna et al. | 424/85 |
| 4,639,434 | 1/1987 | Wenger et al. | 514/11 |
| 4,686,181 | 8/1987 | Doná435 | 7.71/ |
| 4,727,035 | 2/1988 | Mahoney | 436/518 |
| 4,764,503 | 8/1988 | Wenger | 514/11 |
| 5,169,773 | 12/1992 | Rosenthaler et al. | 435/240.27 |

FOREIGN PATENT DOCUMENTS

| | | |
|---|---|---|
| 81105024 | 1/1982 | European Pat. Off. |
| 88103397 | 9/1988 | European Pat. Off. |

OTHER PUBLICATIONS

Fois Romano, Synthesis of a Fluorescent Derivative . . . J of Pharm Sci 80 (4) Apr. 1991, pp. 363–367.
Wolf, B. A.; et al.; Clin. Chem. 1989, 35(1), 120–124.
Vernillet, L.; et al.; Clin. Chem. 1989, 35(4), 608–611.
Ball, P. E.; et al.; Clin. Chem. 1988, 34(2), 257–260.
Schran, H. F.; et al.; Clin. Chem. 1987, 33(12), 2225–2229.
Sanghvi, A.; et al.; Clin. Chem. 1988, 34(9), 1904–1906.
McBride, J. H.; et al.; Clin. Chem. 1989, 35(8), 1726–1730.
Quesniaux, V.; et al.; Clin. Chem. 1987, 33(1), 32–37.
Christians, U.; et al.; Clin. Chem. 1988, 34(1), 34–39.
Donatsch, P.; et al.; J. Immunoassay 1981, 2(1), 19–32.
"Ciclosporin RIA–Kit, Instructions for Use"; Sandoz Ltd., Basle, Switzerland Jun. 1983.
Anonymous; Transplantation Proceedings 1990, 22(3), 1357–1361.
Quesniaux, V. F. J.; et al.; Mol. Immunology 1987, 24(11), 1159–1168.
Cacalano, N. A.; et al.; J. Immunological Methods, 1989, 118, 257–263.
Quesniaux, V.; et al.; Immunology Letters 1985, 9, 99–104.
Traber, R.; et al.; J. Antibiotics 1989, 42(4), 591–597.
Maurer, G.; et al.; Drug Metabolism and Disposition 1984, 12(1), 120–126.
Wisdom, G. B.; Clin. Chem. 1976, 22(8), 1243–1255.
Wenger, R. M.; Helv. Chim. Act. 1983, 66(7), 2308–2321.

Primary Examiner—Michael G. Wityshyn
Assistant Examiner—Ralph Gitomer
Attorney, Agent, or Firm—Theodore J. Leitereg; Janet K. Kaku

[57] ABSTRACT 2-methyl-4-hexene- and 3-methyl-5-heptene-1,2-diol derivatives are disclosed together with methods for preparing such derivatives. Where the derivative is a 2-methyl-4-nexene- or 3-methyl-5-heptene-1,2-diol conjugated to a label, the conjugates are useful in immunoassays. Where the 2-methyl-4-hexene or 3-methyl-5-heptene-1,2-diol is conjugated to an immunogenic carrier, the conjugates may be employed as an immunogen for use in the preparation of antibodies. The label conjugate and the antibodies can be utilized in an immunoassay for the determination or detection of cyclosporin in a sample suspected of containing cyclosporin.

29 Claims, No Drawings

2-METHYL-4-HEXENE-AND 3-METHYL-5-HEPTENE-1,2-DIOL DERIVATIVES

This is a divisional of application Ser. No. 07/093,454, filed Sep. 4, 1987, now U.S. Pat. No. 5,089,390, the disclosures of which are incorporated herein by reference.

BACKGROUND OF THE INVENTION

1. Field of the Invention

The body is capable of both specific immune response and non-specific immune response in dealing with non-self antigens. The body's specific immune response consists mainly in either producing antibodies or receptor cells. Non-specific immune response consists of phagocytosis of bacterial and other particles. Both types of immunity are important in protecting the body from infecting organisms and in maintaining the integrity of the body.

There are a number of circumstances where the body's response to infecting organisms or antigens is deficient. Congenital or acquired immune deficiency, failure to distinguish self and non-self antigens, transplantation of immunologically incompatible organs, destruction of the hemopoietic system where bone marrow tissue replacement is from a non-identical donor (graph versus host disease) are all examples of situations where the body's response is inadequate.

A relatively new drug for treatment of pharmacological immunosuppression is cyclosporin, particularly, cyclosporin A. Cyclosporin A is an extremely hydrophobic cyclic peptide consisting of 11 amino acids with a molecular weight of approximately 1,200. Cyclosporin A suppresses humoral as well as cell mediated immunity in all animal species tested to this point, including humans. The drug may be administered both parenterally or orally. The immunosuppressant effects of cyclosporin A have been demonstrated. Cyclosporin A could be potentially useful in several types of organ transplantation, various autoimmune diseases, and possibly rheumatory arthritis.

In administering a cyclosporin, it is frequently necessary to insure that the blood level of the cyclosporin remains within a certain narrow concentration range in order to insure effective dosage, while avoiding levels which may be toxic or produce undesirable effects. Furthermore, it is often necessary to detect potentially toxic levels of cyclosporin.

It is, therefore, desirable to provide a simple and rapid procedure for determining or detecting the levels of cyclosporin in serum or other physiological fluids. The procedure should provide reproducible values and be specific for the cyclosporin which is measured. Thus the procedure must be capable of distinguishing cyclosporin from other drugs, which would otherwise give an erroneous result in an assay for the detection of a cyclosporin.

2. Brief Description of the Prior Art

A method for the total synthesis of cyclosporins, novel cyclosporins, and novel intermediates and methods for their production are described in U.S. Pat. Nos. 4,396,542 and 4,554,351. A synthesis of enantiomerically pure (2S, 3R, 4R, 6E)-3-hydroxy-4-methyl-2-methylamino-6-octenoic acid starting from tartaric acid is disclosed by Wenger in *Helvetica Chimica Acta* (1983) 66:2308–2321.

SUMMARY OF THE INVENTION 2-methyl-4-hexene- and 3-methyl-5-heptene-l,2-diol (MEHD) derivatives are provided. When the MEHD derivative includes MEHD conjugated to an immunogenic carrier, which is generally a compound of molecular weight greater than 5,000, the MEHD derivative may be utilized as an immunogen to raise antibodies against MEHD. When the MEHD derivative comprises MEHD conjugated to a label, the MEHD derivatives may be utilized in an immunoassay for the detection of cyclosporin.

The MEHD derivatives of the present invention comprise 2-methyl-4-hexene- or 3-methyl-5-heptene-1,2-diol conjugated to a label or a group of molecular weight greater than 5,000 by means of a linking group of from 0–65 atoms other than hydrogen.

The invention further comprises improvements in assays for the determination of cyclosporin in a sample suspected of containing cyclosporin. For example, the assay can comprise the steps of contacting a sample suspected of containing cyclosporin with antibodies for cyclosporin and detecting either directly or indirectly immune complexes of the antibodies and cyclosporin. The improvement of the present invention comprises employing the antibodies raised in response to an immunogenic MEHD derivative.

In another example, the assay for the determination of cyclosporin may comprise the steps of contacting the sample with antibodies for cyclosporin and a conjugate of a label and a compound recognized by the antibodies. The method further comprises detecting either directly or indirectly immune complexes of the label conjugate and the antibodies. The improvement of the present invention comprises employing as the label conjugate an MEHD derivative which is MEHD conjugated to a label.

The invention also includes certain improvements in assay reagents for use in the determination of cyclosporin in a sample suspected of containing cyclosporin. Furthermore, the invention includes kits for conducting an assay for the determination of cyclosporin. The present invention also includes methods for preparing MEHD derivatives.

DESCRIPTION OF THE SPECIFIC EMBODIMENTS

Novel compounds are provided which are derivatives of 2-methyl-4-hexene- and 3-methyl-5-heptene-l,2-diol (MEHD). The MEHO derivatives of the present invention in their broadest aspect comprise compounds having 2-methyl-4-hexene linked to a label or a group of molecular weight greater than 5,000. The linking group contains from 0–65 atoms other than hydrogen. The compounds of the invention find use in immunoassays as reagents for use in the detection or determination of cyclosporin or may be used to raise antibodies that may be utilized as reagents in such determinations.

For the most part, compounds of this invention will have the following formula:

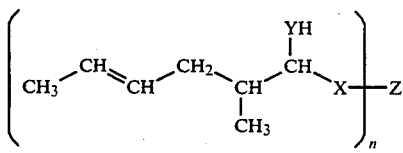

(I)

wherein:
X is a linking group of from 0–65, preferably 0–35, atoms other than hydrogen. When X contains more than 0 atoms, the atoms are independently selected from the group consisting of oxygen, sulfur, phosphorous, nitrogen, silicon, carbon, and halogen, and can include such functionalities as, for example, ether, oxocarbonyl, non-oxocarbonyl such as esters, amides, carbamates, sulfone, sulfoxide, phosphate, silicates, and the like, or combinations thereof, preferably an ether, for example, —CH$_2$OA wherein A is a linking group of 0 to 63 atoms, preferably 0–33 atoms, other than hydrogen. When A contains more than 0 atoms, at least 1 atom is a carbon atom and A is bonded to —CH$_2$O through a carbon atom and is bonded to Z. Preferably A contains a non-oxocarbonyl that is bonded to Z, preferably A is C=W wherein W is oxygen, sulfur, or NR wherein R is hydrogen or lower alkyl (C1 to C5), preferably wherein C=W is bonded to NRX', wherein X' is a linking group having from 0 to 60 atoms other than hydrogen, preferably 0 to 30 atoms other than hydrogen. When X' contains more than 0 atoms the atoms are selected from the group consisting of oxygen, sulfur, phosphorus, nitrogen, silicon, and carbon. The term non-oxocarbonyl intends a carbonyl group substituted with at least one heteroatom; for the purposes of this disclosure non-oxocarbonyl shall include but not be limited to

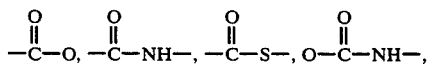

and the iminocarbonyl and thiocarbonyl analogs thereof.

Z is a luminescent label or a group of molecular weight greater than 5,000, more preferably greater than 10,000, preferably, the luminescent label is selected from the group consisting of fluorogenic substrates, fluorescers, chemiluminescers, and fluorescent particles and the group of molecular weight greater than 5,000 is selected from the group consisting of poly(amino acids) such as enzymes and immunogenic carriers selected from the group consisting of immunogenic poly(amino acids), lipopolysaccharides and particles, or Z can be a ligand for which a receptor is available, such as biotin or a hapten, such as an organic molecule of less than 1000 molecular weight.

Y is oxygen or sulfur, preferably oxygen; and n is a number from 1 up to the molecular weight of Z divided by 1,000, preferably divided by 4,000, preferably 1 when Z is a luminescent label and 2 to 20, usually 3 to 10 when Z is a poly(amino acid).

The above compounds include both optically active and optically inactive isomers. The optically active isomers where X is —CH$_2$OA— include (2S, 2S) or (2S, 2R) or (2R, 2S) or (2R, 2R), and also include the cis- and trans- isomers.

A particular embodiment of the present invention includes compounds of the formula, which are derivatives of 3-methyl-5-neptene-1,2-diols:

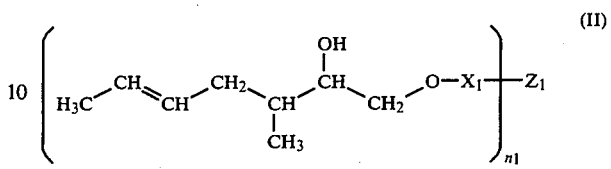

wherein:
X$_1$ is a linking group of from 0–35 atoms other than hydrogen. When X$_1$ contains more than 0 atoms, at least 1 atom is a carbon atom and the remaining atoms are each independently selected from the group consisting of carbon, oxygen, nitrogen, and sulfur, wherein the linking group is bound to 0 through a carbon atom and is bonded to Z, and wherein the linking group can include a functionality such as ether, nonoxocarbonyl, preferably amide, including the nitrogen and sulfur analogs, preferably a linking group of from 2 to 10 atoms other than hydrogen wherein the group includes an amide functionality including carbamate.

Z$_1$ is a poly(amino acid) of molecular weight greater than 5,000, which is immunogenic or an enzyme; and n$_1$ is a number from 1 up to the molecular weight of Z$_1$ divided by 1,000, preferably divided by 4,000, preferably 2 to 20, more preferably 3 to 10.

Another particular embodiment of the present invention includes compounds of the formula:

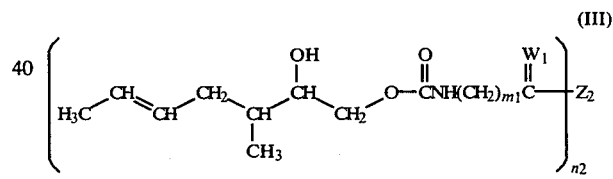

wherein:
W$_1$ is O, S, or NH, preferably O;
m$_1$ is 0 to 10, preferably 1 to 5;
Z$_2$ is a polyamino acid, which is an immunogenic or an enzyme; or biotin or a hapten;
n$_2$ is a number from 1 up to the molecular weight of Z$_2$ divided by 1,000, preferably divided by 4,000.

The group having a molecular weight greater than 5,000 includes polyamino acids, lipopolysaccharides, and particles. Such a group can be a label or an immunogenic carrier.

The poly(amino acids) will generally range from about 5,000 molecular weight, having no upper molecular weight limit, normally being less than 10,000,000, usually not more than about 600,000 daltons. There will usually be different ranges, depending on whether an immunogen or an enzyme is involved, with immunogens ranging from about 5,000 to 10$^7$, usually from about 20,000 to 600,000, and more usually from about 25,000 to 250,000 molecular weight; while enzymes will generally range from about 10,000 to 600,000, more usually from about 10,000 to 300,000 molecular weight. There will usually be at least about one MEHD conjugate group per 150,000 molecular weight, more usually at least one conjugate group per 50,000 molecular weight. With intermediate molecular weight immunogens (35,000 to 1,000,000), the number of conjugate groups will generally be from about 1 to 200, more usually from 2 to 100. With lower molecular weight immungens below 35,000, the number of conjugate groups will generally be in the range of from about 1 to 10, usually in the range of 1 to 5.

Various protein types may be employed as the poly(amino acid) immunogenic material. These types include albumins, serum proteins, e.g., globulins, ocular-lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be utilized.

The immunogenic carrier can also be a polysaccharide, which is a high molecular weight polymer built up by repeated condensations of monosaccharides. Examples of polysaccharides are starches, glycogen, cellulose, carbohydrate gums, such as gum arabic, agar, and so forth. The polysaccharide can also contain polyamino acid residues and/or lipid residues.

The immunogenic carrier can also be a nucleic acid either alone or conjugated to one of the above mentioned poly(amino acids) or polysaccharides.

The immunogenic carrier can also be a particle. The particles are generally at least about 0.02 microns and not more than about 100 microns, usually at least about 0.05 microns and less than about 20 microns, preferably from about 0.3 to 10 microns diameter. The particle may be organic or inorganic, swellable or non-swellable, porous or non-porous, preferably of a density approximating water, generally from about 0.7 to about 1.5 g/ml, and composed of material that can be transparent, partially transparent, or opaque. The particles can be biologic materials such as cells and microorganisms, e.g., erythrocytes, leukocytes, lymphocytes, hybridomas, streptococcus, *staphylococcus aureus, E. coli,* viruses, and the like. The particles can also be particles comprised of organic and inorganic polymers, liposomes, latex particles, phospholipid vesicles, chylomicrons, lipoproteins, and the like.

The polymers can be either addition or condensation polymers. Particles derived therefrom will be readily dispersible in an aqueous medium and may be adsorptive or functionalizable so as to bind to MEHD, either directly or indirectly through a linking group.

The particles can be derived from naturally occurring materials, naturally occurring materials which are synthetically modified and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The particles will usually be Polyfunctional and will be bound to or be capable of binding to MEHD. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.* (1970) 245:3059.

The poly(amino acid) can be an enzyme that is part of a signal producing system. The function of the signal producing system is to produce a product which provides a detectable signal related to the amount of bound and unbound label. Where enzymes are employed, the involved reactions will be, for the most part, hydrolysis or redox reactions.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued Jul. 10, 1979, the appropriate portions of which are incorporated herein by reference.

The enzyme or coenzyme employed provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980 columns 10 to 14, which disclosures are incorporated herein my reference.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference.

When a single enzyme is used as a label, such enzymes that may find use are hydrolases, transferases, lyases, isomerases, ligases or synthetases and oxidoreductases, preferably hydrolases. Alternatively, luciferases may be used such as firefly luciferase and bacterial luciferase. Primarily, the enzymes of choice, based on the I.U.B. classification are: Class 1. Oxidoreductases and Class 3. Hydrolases; particularly in Class 1, the enzymes of interest are dehydrogenases of Class 1.1, more particularly 1.1.1, 1.1.3, and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the oxidases, glucose oxidase is exemplary. Of the peroxidases, horse radish peroxidase is illustrative. Of the hydrolases, alkaline phosphatase, β-glucosidase and lysozyme are illustrative.

Those enzymes which employ nicotinamide adenine dinucleotide (NAD) or its phosphate (NADP) as a cofactor, particularly the former can be used. One preferred enzyme is glucose-6-phosphate dehydrogenase.

A label may be any molecule conjugated to an analyte or an antibody, or to another molecule. In the subject invention, the label can be a member of the signal producing system that includes a signal producing means. The label may be isotopic or nonisotopic, preferably nonisotopic. By way of example and not limitation, the label can be a catalyst such as an enzyme, a co-enzyme, a chromogen such as a fluorescer, dye or chemiluminescer, a dispersible particle that can be non-magnetic or magnetic, a solid support, a liposome, a ligand, a hapten, and so forth.

The signal producing system may have one or more components, at least one component being a label. The signal producing system includes all of the reagents required to produce a measurable signal including signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

The signal producing means is capable of interacting with the label to produce a detectable signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

The signal producing system including the label can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/ml, and composed of material that can be transparent, partially transparent, or opaque. Generally, particles utilized as a label will have similar characteristics to those described above for an immunogenic carrier.

Many different types of particles may be employed for modulating light emission. Of particular interest are carbon particles, such as charcoal, lamp black, graphite, colloidal carbon and the like. Besides carbon particles metal sols may also find use, particularly of the noble metals, gold, silver, and platinum. Other metal-derived particles may include metal sulfides, such as lead, silver or copper sulfides or metal oxides, such as iron or copper oxide.

Fluoresceinated latex particles are taught in U.S. Pat. No. 3,853,987 and are available commercially as Coraspheres from Covalent Technology Corp.

The label can also be fluorescent either directly or by virtue of fluorescent compounds or fluorescers bound to a particle in conventional ways. The fluorescers will usually be capable of, or functionalized to render them capable of, being bound to MEHD or to particle.

The fluorescers of interest will generally emit light at a wavelength above 350 nm, usually above 400nm and preferably above 450 nm. Desirably, the fluorescers have a high quantum efficiency, a large Stokes shift and are chemically stable under the conditions of their conjugation and use. The term luminescent label is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminostilbenes imines, anthracenes, oxacarboxyanine, merocyanine, 3-aminoequilenin, perylene, bis-benzoxaole, bis-p-oxazolyl benzene, 1,2-benzophenazine, retinol, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference.

Energy absorbers or quenchers can be employed either separately or in conjunction with one another. The absorber or quencher can additionally be bound to a solid insoluble particle of at least about 50nm in diameter. When the distance between the absorber and the quencher resulting from specific binding events (such as antibody-antigen binding), the fluorescence of the absorber is quenched by the quencher. The quencher may be the same or different, usually different, from the fluorescer.

An alternative source of light as a detectable signal is a chemiluminescent source, and, therefore, a label can be a chemiluminescent compound. The chemiluminescent source involves a compound which becomes electronically excited by a chemical reaction and may then emit light which serves as the detectable signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino analog of the above compound. Other members of the family include the 5-amino-6,7,8-trimethoxy- and the dimethylamine-[ca]-benzo analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino- and para-methoxy-substituents. Chemiluminescence may also be obtained with oxalates, usually oxalyl, active esters, e.g., p-nitrophenyl and a peroxide, e.g., hydrogen peroxide, under basic conditions. Alternatively, luciferins may be used in conjunction with luciferase or lucigenins.

An example of the preparation of a compound of the invention wherein X (Formula I) includes a —CH$_2$O— group is outlined in the following schematic:

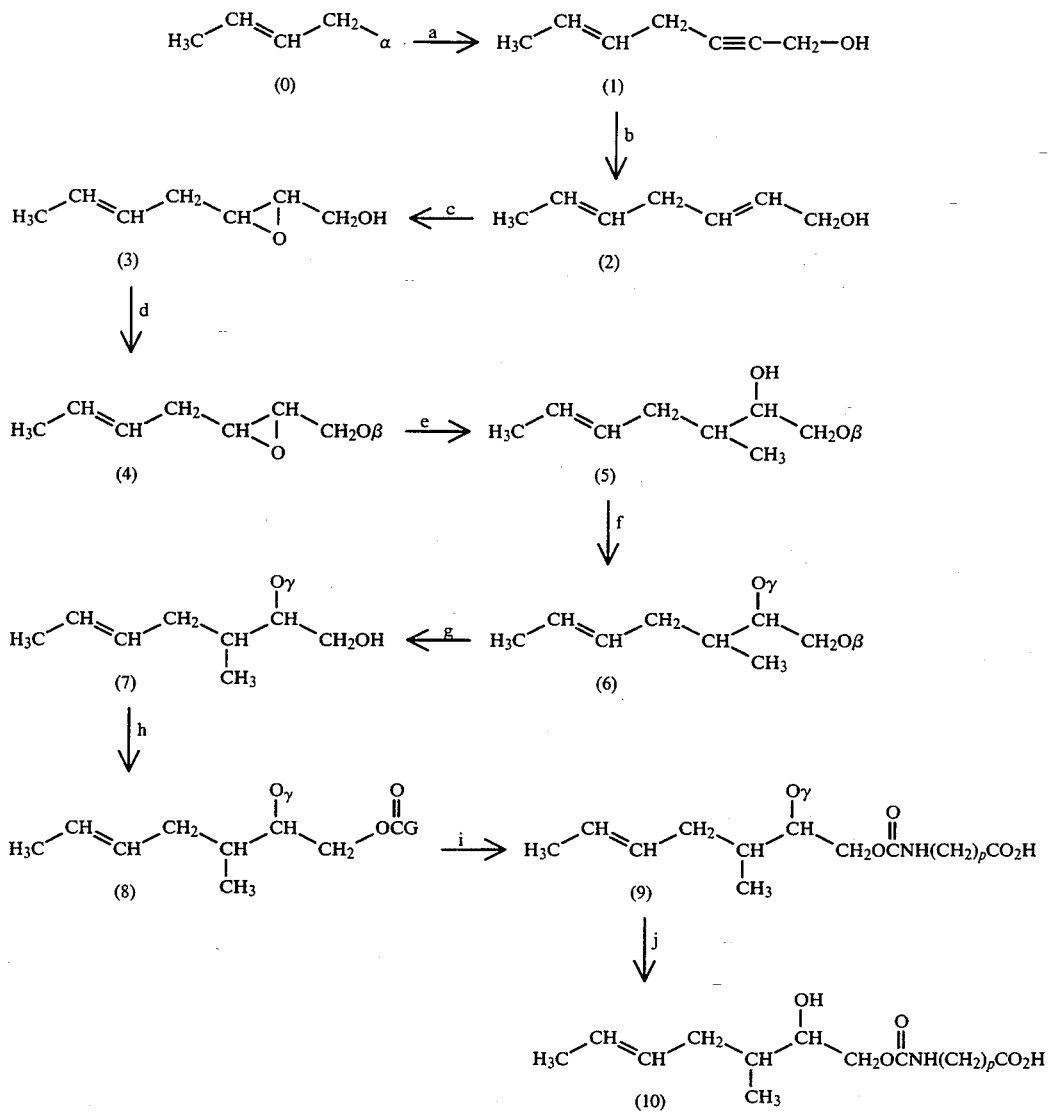

wherein:
a) α is halogen, preferably bromine. Compound 0 is reacted under suitable anhydrous conditions with an appropriate organometallic reagent to prepare Compound 1. In the example shown, the organometallic reagent is BrMgOCH$_2$C≡CMgBr. However, other organometallic reagents can be utilized.

b) Compound 1 is treated under reducing conditions and reagents, such as lithium aluminum hydride in an anhydrous medium to reduce the triple bond and give Compound 2.

c) Compound 2 is treated to form the epoxide of Compound 3. Such treatment includes contact with, for example, a hydroperoxide such as an alkyl hydroperoxide, e.g., tert-butyl hydroperoxide.

d) Compound 3 is derivatized to protect the terminal hydroxy functionality. Accordingly, β is a removable protecting group such as a substituted silyl group, e.g., diphenyl t-butylsilyl. Compound 3 is treated under appropriate silylating conditions with a substituted silyl halide, e.g., diphenyl t-butylsilyl chloride, to produce compound 4.

e) Compound 4 is treated under conditions for methylating the epoxide functionality. Accordingly, 4 can be reacted under appropriate conditions with, e.g., (CH$_3$)$_2$CuCNLi$_2$ to give Compound 5.

f) The free hydroxy group of Compound 5 is protected with a removable protecting group γ such as, for example, alkoxyalkyl group (C2 to C8). Accordingly, 5 is reacted with, e.g., CH$_2$=CH—OC$_2$H$_5$, or homolog thereof, under appropriate conditions to give Compound 6.

g) Protecting group β of Compound 6 is removed under appropriate conditions to give Compound 7.

h) The free hydroxy group of Compound 7 is treated with an activated formate derivative $$\text{E} \overset{\overset{\text{O}}{\|}}{\text{C}} \text{G}$$

wherein E and G are leaving groups such as aryloxy, halo, etc., to provide an activated formate ester capable of forming an amide by reaction with an amino group; such activated formate ester groups include, e.g., N-oxy-succinimide, p-nitrophenoxy, and the like. Thus, 7 is reacted under suitable condition with, for example, $$\overset{\text{ECG,}}{\underset{\text{O}}{\|}}$$

wherein E is halogen and G is p-nitrophenoxyl to give Compound 8.

i) Compound 8 is reacted under appropriate conditions with a compound containing an amino group such as, for example, $H_2N(CH_2)_pCO_2H$, wherein p is 1 to 20, to give Compound 9.

j) The hydroxy protecting group of Compound 9 is removed under appropriate conditions such as treatment with an acidic medium, e.g., dilute mineral acid.

Compound 10 can then be utilized to prepare the derivatives of the present invention by reaction under suitable conditions. For example, enzyme conjugates of Compound 10 can be prepared by forming an activated ester of the carboxyl group of Compound 10 and reacting Compound 10 with the appropriate enzyme to yield an amide enzyme derivative of Compound 10. Other derivatives of Compound 10 can be prepared in a manner similar to the enzyme derivatives. In such a way one can prepare derivatives of Compound 10 having a luminescent label, ligand label, immunogenic poly(amino acid), polysaccharide, particle, and the like. Variations in the above scheme can be made by those skilled in the art to produce compounds falling within the scope of the present invention.

Another aspect of the present invention includes antibodies prepared in response to Compound 1 wherein Z is an immunogenic carrier. Furthermore, the present invention includes conjugates of such antibodies and a label.

An antibody is an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera from which the immunoglobulin can be separated by known techniques (polyclonal) or by preparing continuous hybrid cell lines and collecting the secreted protein (monoclonal). Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like.

Monoclonal antibodies can be obtained by the process discussed by Milstein and Kohler and reported in Nature, 256:495-497, 1975. The details of this process are well known and will not be repeated here. However, basically it involves injecting a host, usually a mouse or other suitable animal, with an immunogen. The mouse is subsequently sacrificed and cells taken from its spleen. Alternatively, the host may be unsensitized spleen cells, which are sensitized to the immunogen in vitro. The resulting cells are fused with myeloma cells. The result is a hybrid cell, referred to as a "hybridoma" that can be cultured in vitro. The population of hybridomas is screened and manipulated so as to isolate individual clones each of which secretes a single antibody to the antigen.

The antibodies of the present invention recognize the cyclosporins including cyclosporin A and derivatives and metabolites of cyclosporins. Cyclosporin A has the following structure:

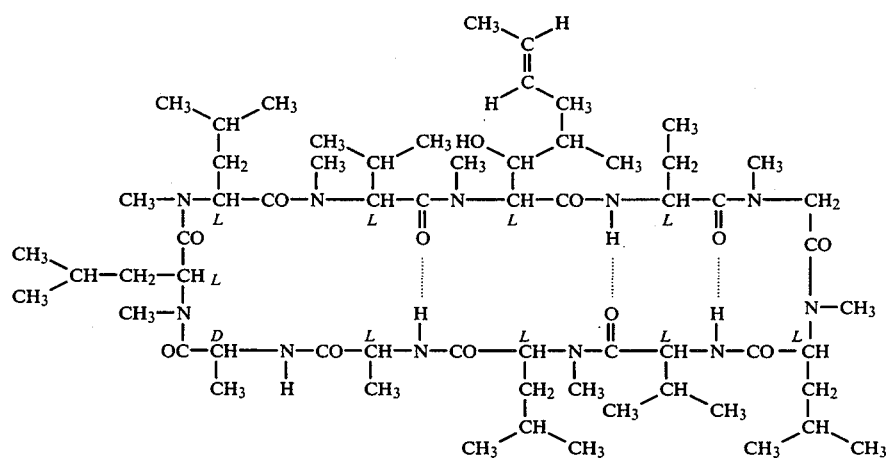

The antibodies of the present invention are capable of specifically recognizing cyclosporin and closely related compounds containing the unmodified $C_9$ amino acid.

Conjugates of the antibodies of the present invention and a label can be prepared by methods already descended above for the conjugation of poly(amino acids) to HEHD.

The antibodies or the present invention can be utilized in the determination of cyclosporin in a sample suspected of containing cyclosporin. The assay can comprise the steps of contacting the sample with antibodies for cyclospoin and detecting either directly or indirectly immune complexes of the antibodies and cyclosporin. The improvement provided in the present invention is the utilization of the present antibodies as the antibodies for cyclosporin. The immune complexes are detected directly, for example, where the antibodies employed are conjugated to a label. The immune complex is detected indirectly by examining for the effect of immune complex formation in an assay medium, on a signal producing system or by employing a labeled antibody that specifically binds to an antibody of the invention.

In another configuration of an assay for the determination of cyclosporin in a sample suspected of containing cyclosporin, the sample is contacted with antibodies for cyclosporin and a conjugate of this invention recognized by the antibodies. The method further includes detecting either directly or indirectly immune complexes of the conjugate and the antibodies. The improvement provided in the present invention is employing as the label conjugate Compound 1 wherein Z is a label.

The present assay invention has application to all immunoassays for cyclosporin. The assay can be performed either without separation (homogeneous) or with separation (heterogeneous) of any of the assay components or products. Exemplary of heterogeneous assays are enzyme linked immunoassays such as the enzyme linked immunosorbent assay (ELISA), see "Enzyme-Immunoassay" by Edward T. Maggio, CRC Press Incorporated, Boca Raton, Fla., 1980. Homogeneous immunoassays are exemplified by enzyme multiplied immunoassay techniques (e.g. see U.S. Pat. No. 3,817,817), immunofluorescence methods such as those disclosed in U.S. Pat. No. 3,993,345, enzyme channeling techniques such as those disclosed in U.S. Pat. No. 4,233,402, and other enzyme immunoassays as discussed in Maggio, supra.

The assay for the analyte will normally be carried out in an aqueous buffered medium at a moderate pH, generally that which provides optimum assay sensitivity.

The aqueous medium may be solely water or may include from 0 to 40 volume percent of a cosolvent. The pH for the medium will usually be in the range of about 4 to 11, more usually in the range of about 5 to 10, and preferably in the range of about 6.5 to 9.5. The pH will usually be a compromise between optimum binding of the binding members and the pH optimum for other reagents of the assay such as members of the signal producing system.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from about 5° to 45° C., more usually from about 15° to 40° C. Temperatures during measurements will generally range from about 10° to 50° more usually from about 15° to 40° C.

The concentration of cyclosporin which may be assayed will generally vary from about $10^{-5}$ to $10^{-13}$M, more usually from about $10^{-7}$ to $10^{-11}$M. Considerations, such as whether the assay is qualitative, semiquantitative or quantitative, the particular detection technique and the concentration of the cyclosporin will normally determine the concentrations of the various reagents.

While the concentrations of the various reagents in the assay medium will generally be determined by the concentration range of interest of cyclosporin, the final concentration of each of the reagents will normally be determined empirically to optimize the sensitivity of the assay over the range. That is, a variation in concentration of cyclosporin which is of significance should provide an accurately measurable signal difference.

While the order of addition may be varied widely, there will De certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation-step may be involved subsequent to each addition, generally ranging from about 30 seconds to 6 hours, more usually from about 2 minutes to 1 hour.

In a homogeneous assay after all of the reagents have been combined either simultaneously or sequentially, the effect of the assay medium on the signal is determined. The effect of the assay medium on the signal is related to the amount of cyclosporin in the sample tested. For example, in the enzyme multiplied immunoassay technique for the detection of cyclosporin, a sample suspected of containing cyclosporin is combined either simultaneously or sequentially with an antibody of the present invention and a conjugate of an enzyme and an MEHD derivative such as compound I wherein Z is an enzyme. A particularly preferred enzyme is glucose-6-phosphate dehydrogenase. The cyclosporin in the sample and the MEHD-enzyme conjugate compete for sites on the antibody. The difference in enzyme activity resulting from the presence or absence of cyclosporin in the sample is then determined By known techniques and is related to the amount of cyclosporin in the sample.

Heterogeneous assays usually involve one or more separation steps. The heterogeneous assay can be competitive or non-competitive. In the competitive assay an antibody of the invention can be bound to a support, which is then contacted with a medium containing sample and a conjugate of MEHD and an enzyme such as-compound I wherein Z is an enzyme label. Cyclosporin in the sample competes with the conjugate for the sites on the antibody bound to the support. After separation of the support and the medium, the enzyme activity of the support or the medium can be determined by conventional techniques and is related to the amount of cyclosporin in the sample.

In another competitive heterogeneous approach, an antibody of the invention is bound to a support. A medium is prepared containing a sample suspected of containing cyclosporin and a conjugate of MEHD and a small organic molecule (molecular weight less than 1500) such as biotin (compound I wherein Z is biotin). Cyclosporin and the conjugate compete for the antibody sites. After a period of time, the support is separated from the medium, washed, and contacted with a second medium containing a receptor or binding partner for the small organic molecule bound to a label such as an enzyme. If the small organic molecule is biotin, the support can be contacted with avidin bound to an enzyme. The support is separated from the second medium and enzyme activity of either the support or the second medium is determined by conventional methods. The enzyme activity is related to the amount of cyclosporin in the sample.

An example of a non-competitive approach is a sandwich assay involving two antibodies, one of which can be labeled and further one of which can be bound to a support or caused to become bound to a support.

In another embodiment, agglutination can be utilized to determine the presence or amount of cyclosporin in a sample. Antibodies raised in response to compound I wherein Z is an immunogenic carrier can be conjugated to particles. Another particle conjugate that can be employed is compound I where Z is a particle. In one approach, a sample suspected of containing cyclosporin can be combined with an antibody-particle conjugate mentioned above. After an appropriate incubation, the extent of agglutination of the particles due to the presence of cyclosporin can be determined directly. On the other hand, the particles can be separated from the medium, washed, and combined with a conjugate of a particle and MEHD. Agglutination can then be determined as a measure of the amount of cyclosporin in the sample. The above description exemplifies only two of many agglutination protocols that may be carried out utilizing the compounds of the invention.

One aspect of the present invention includes compounds of the formula which can be utilized as intermediates in the preparation of the MEHD derivatives of the invention:

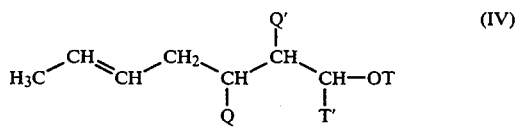

(IV)

wherein:

Q is a bond or lower alkyl (C1 to C5);

Q' is OH or $OR_1$ wherein $R_1$ is lower alkyl, alkoxyalkyl (C2 to C8) such as ethoxyethyl, when Q is a bond Q' can be taken together with Q and an oxygen atom to form a three-membered ring;

T is a removable protecting group such as silicon having substituents each independently selected from the group consisting of aryl (6–20 atoms) such as phenyl, alkaryl (7–25 atoms) such as benzyl, and lower alkyl such as t-butyl, or $W_2CY_{20}R_2$ wherein $W_2$ is O, S, or NH, $Y_2$ is O or S, and $R_2$ is phenyl, p-nitrophenyl, or $HN(CH_2)_qCO_2H$ wherein q is 1 to 20 such as . $H_2NCH_2CO_2H$; or T can be a group removable by metal reduction, such as benzyl, naphthylmethyl, and the like; and T' is hydrogen or, when T is lower alkyl or aryl, T' can be OT, wherein the T's can be linked together to form a five or six-membered ring.

To enhance the versatility of the subject invention, the reagents can be provided in packaged combination, in the same or separate containers, so that the ratio of the reagents provides for substantial optimization of the method and assay. The kit comprises as one reagent an antibody raised in response to Compound I wherein Z is an immunogenic carrier. This antibody can be labeled or unlabeled. The kit may also include Compound I wherein Z is a label. The kit can further include other separately packaged reagents for conducting an assay including members of the signal producing system, other antibodies either labeled or unlabeled, supports, ancillary reagents, and so forth.

A support is a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass, ceramics, metals, and the like.

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

EXAMPLE 1

Preparation of (E)-Hept-5-ene-2,yn-1-ol

Trans crotyl bromide (59.4g) was reacted with a solution of prop-2-yn-1-ol (22.4g) and two equivalents (eq.) of ethylmagnesium bromide to give mostly (E)-hept-5-ene-2-yn-1-ol (1) as a colorless oil (40g, 80%), b.p. 71°–71.5° C. (20 mm Hg). NMR ($CDCl_3$, δ): 1.6 (dd, $CH_3$), 2.4 (t, OH), 2.9 (m, 2H), 4.2 (m,2H), 5.50 (m, 2H). I.R. (neat) 3350s, 3050m, 2940s, 2900s, 2300w, 2250w, 1650w, $cm^{-1}$.

EXAMPLE 2

Preparation of (E,E)-hepta-2,5.-diene-1-ol

Compound 1 (22.0 g) was reacted with lithium aluminum hydride (23.0 g, 3 eq), in ether to give (E,E)-hepta-2,5-diene-1-ol (2) as a colorless oil (21 g) b.p. 98°–100° C. (35 mm Hg). NMR ($CDCl_3$, δ): 1.6 (dd, 3H), 1.9 (b, OH), 2.7 (m, 2H), 4.1 (m, 2H), 5.4 (m, 2H), 5.7 (m, 2H). IR (neat) 3350s, 3025m, 2980m, 2950s, 2925s, 2900s, 2850s, 1670w, 1430m, $cm^{-1}$.

EXAMPLE 3

Preparation of Hept-2S,3S-epoxy-5(E)-ene-1-ol

Compound 2 (14.5 g) was epoxidized using 5% titanium (IV) isopropoxide (1.98 g) and t-butylhydroperoxide and 5% L(+) diethyl tartarate (2.10 g) and 4A° molecular sieves to give hept-2S,3S-epoxy-5(E)-ene-1-ol (3) as a low melting solid 14.4 g, m.p. 20°–25° C. NMR ($CDCl_3$, δ): 1.6 (m, 3H), 2.3 (m, 2H), 2.9 (m, 2H), 3.3–4.1 (m, 2H, OH), 5.5 (m, 2H). IR (neat) 3400s, 3050m, 2975s, 2925s, 2850s, $cm^{-1}$, $[\alpha]_D^{25} = -27$ (C=1, $CHCl_3$).

EXAMPLE 4

Preparation of the t-Butyl Diphenylsilyl Ether of Hept-2S ,3S, -epoxy-5(E)-ene-1-ol Compound 3 (14.2 g) was reacted with t-butyl diphenyl chlorosilane (33.8 g) and imidazol (16.73 g) in DMF to give the silane derivative 4 ($\beta$=($C_6H_5$)$_2$SiC($CH_3$)$_3$) (40 g) as a colorless liquid. NMR ($CDCl_3$, δ): 1.1(s, 9H), 1.7 (m, 3H), 2.3 (m, 2H), 2.7–3.1 (m, 2H), 3.8 (d, 2H), 5.4–5.8 (m, 2H), 7.3–7.9 (m, 10H). IR (neat); 3100m, 3075m, 3000m, 2970s, 2940s, 2900w, 2850s, 1590w, 1470w, 1460m, 1430s, $cm^{-1}$, $[\alpha]_D^{25} = -6.4$ (C=1, $CHCl_3$).

EXAMPLE 5

Preparation of 2R, 3R, 5E-2-ol-3-methyl-5-heptene-1-t-butyl diphenyl silyl ether Compound 4 (14.62 g) was reacted with lithium dimethyl cyano cuprate (prepared from 8.0 g of CaCN) (2eq) in ether:THF mixture to give compound 5 ($\beta$=($C_6H_5$)$_2$SiC($CH_3$)$_3$) as a colorless oil which was purified on silica gel; ether:hexane (2:98) was used as eluting solvent. NMR ($CDCl_3$,δ): 0.8(d, 3H) 1.1 (s, 9H), 1.6(d, 3H), 1.8 ∝ 2.4 (m. 2H), 2.6 (d, —OH), 3.4–3.8 (m, 3H), 5.4 (m, 2H), 7.3–7.8 (m, 10H). IR (neat): 3575w, 3450w, 3075w, 3050w, 3010w, 3000w, 2970s, 2940s, 2900m, 2860s, 1590w, 1470m, 1460m, 1406s, cm$^{-1}$, $[\alpha]_D^{25} = -8.1$ (C=1, CHCl$_3$).

EXAMPLE 6

Preparation of 2R, 3R,5E-2-(1-ethoxymethoxy)-3-methyl-5-heptene-1-t-butyl diphenyl silyl ether Compound 5 ($\beta$=(C$_6$H$_5$)$_2$SiC(CH$_3$)$_3$) (50 g) was reacted with ethyl vinyl ether (11.5 g) and pyrdinium p-toluene sulfonate (0.260 mg) to give compound 6 ($\gamma$=—CH(CH$_3$)OC$_2$H$_5$ ($\beta$=(C$_6$H$_5$)$_2$SiC(CH$_3$)$_3$)) as a colorless oil which was a mixture of 1:1 diastereomers (5.0 g). NMR(CDCl$_3$,$\delta$): 0.8 (dd, 3H), 1.2 (dq, 3H), 1.3 (d, 3H), 1.6 (d, 3H), 1.7–2.2 (m, 2H), 3.3–3.8 (m, 5H), 4.6 (q, ½H), 4.8 (q, ½H), 5.4 (m, 2H), 7.3–7.8 (m, 10H). IR (neat): 3075 m, 3050m, 3010m, 2960s, 2940s, 2900s, 2850s, 1590w, 1470m, 1460m, 1430s, cm$^{-1}$. $[\alpha]_D^{25} = -0.71$ (C=1, CHCl$_3$).

EXAMPLE 7

Preparation of 2R,3R,5E-2-(1'-ethoxymethoxy)-3-methyl-5-heptene-1-ol

Compound 6 ($\gamma$=—CH(CH$_3$)OC$_2$H$_5$) (5.0 g) was reacted with tetrabutyl ammonium fluoride 23 ml (1M in THF, 2 eq.) in THF to give Compound 7 ($\gamma$=CH(CH$_3$)OC$_2$H$_5$) as a colorless oil 2.3 g and a mixture of 1:1 diastereomers. Physical data and IR, NMR spectra are identical with the reported data in the literature, Roger Wenger, *Helvetica Chemica Acta*, 2308 (1983).

EXAMPLE 8

Preparation of 2R, 3R, 5E-2(1'-ethoxymethoxy)-3-methyl-5-hepten-1-p-nitrophenyl formate Compound 7 ($\gamma$=—CH(CH$_3$)OC$_2$H$_5$) (216 mg) was reacted with p-nitrophenylchloroformate (230 mg) (1.1 eq.) in ether and triethyl amine (1.2 eq) at 0° to give the carbamate 8 ($\gamma$=—CH(CH$_3$)OC$_2$H$_5$, G=OC$_6$H$_4$NO$_2$) which after evaporation of the solvent was used without further purification.

EXAMPLE 9

Preparation of 2R,3R, 5E-2-(1'-ethoxymethoxy )-3-methyl-5-hepten-1-glycyl carbamate Carbamate 8 ($\gamma$=—CH(CH$_3$)OC$_2$H$_5$, G=OC$_6$H$_4$NO$_2$) was dissolved in DMF and added to a solution of glycine in water at pH=8.5 at room temperature for 24 hours to give Compound 9 ($\gamma$=—CH(CH$_3$)OC$_2$H$_5$, p=1) (150 mg) in 50% yield as a semi-solid. NMR (CDCl$_3$, $\delta$): 0.8 (dd, 3H), 1.2 (2T, 3H), 1.4 (d, 3H), 1.7 (d, 3H), 1.8 (m, 2H), 2.1 (m, 1H), 3.5 (m, 6H), 4.0 (d, 2H), 4.1–4.4 (m, 2H), 4.8 (m, 1H) and 5.4 (m, 2H).

EXAMPLE 10

Preparation of 2R,3R,5E-2-ol-3-methyl-5-hepten-1-glycyl carbamate

Compound 9 ($\gamma$=CH(CH$_3$)OC$_2$H$_5$, p=1) 100mg was reacted with a hydrochloric acid (1N) in THF for one hour to give Compound 10 (p=1) as a white crystal (m.p. 101°–102° C.) in 95% yield. NMR (CDCl$_3$, $\delta$): 0.8 (d, 3H), 1.6 (d, 3H), 1.8 (m, 1H), 2.2 (m, 2H), 3.4 (m, 1H), 3.7 (d, 2H), 3.8–4.1 (m, 2H) and 5.4 (m, 2H). IR (KBr): 3400 bm, 3000 bm, 1730 s, 1680 S, 1540 s, 1460 w, 1450 w, 1410 m, 1220 s, 1000 m cm$^{-1}$.

EXAMPLE 11

Conjugation of Compound 10 (p=1) to G6PDH

Compound 10 (p=1) (24.5 mg) was reacted with N-hydroxy succinimide (11.5 mg) in DMF overnight at 0°–5° C. and then was added portionwise to a solution of glucose-6-phosphate dehydrogenase (G6PDH) and glucose-6-phosphate (G6P) and NADH in a Tris base buffer at pH 8.0 and ice bath temp. Two samples at 46% and 70% deactivation of enzyme were prepared. The samples were purified on a Sephadex G-25 column using Tris base buffer pH 8.0. The hapten numbers were 5 and 10 for 46% and 70% deactivation of enzyme.

EXAMPLE 12

Conjugation of Compound 10 (p=1) to Keyhole Limpet Hemocyanin (KLH)

To a stirred solution of radioactive labeled Compound 10 (p=1) (24.5 mg, 0.1 mmol, 2.19×10$^7$ CPm/mmol) in DMF (2 ml) was added N-hydroxy succinimide (11.7 mg, 0.11 mmol). The mixture was then cooled in an ice bath and dicyclohexyl carbodiimide (DCC) (20.6 mg, 0.11 mmol) was added. The mixture was stirred overnight in a cold room (+5° C.). The reaction mixture was then filtered and was added to a suspension of KLH (910) mg in sodium borate buffer (30 ml, pH=8.5). The mixture was stirred in the cold room overnight and then it was concentrated to half its volume (Amicon filter, PM 30,000). The mixture was purified on a Sephadex G-50 column using water as eluting solvent. The protein fraction was then collected and dialyzed in water and then was lyophilized to give 500 mg of the protein. The hapten/protein ratio was determined to be 170.

EXAMPLE 13

Preparation of Monoclonal Antibodies

The standard hybridoma procedures used have been described in detail by Hurrell (Hurrell, J. G. R. "Monoclonal Hybridoma Antibodies: Techniques and Applications" (1982) CRC Press, Boca Raton, Fla. 33431).

The cell lines used were P3-X63-AG8.653 myeloma cells and spleen cells from 4-Balb/c mice immunized with the conjugate of Example 12, namely, Compound 10 (p=1)-KLH conjugate, as an immunogen. Mice received 3–100 $\mu$g doses of the immunogen in Freund's adjuvant by intraperitoneal (IP) injection at monthly intervals, followed by a final IP booster in saline three days before the fusion. Cells were fused using polyethylene glycol and then were suspended in HAT media and distributed into 20 96-well microplates. Media in the wells were replenished four days later, and the resultant hybridomas were screened for specific antibodies when the wells were half-confluent with cells, seven days after the fusion.

Cell lines selected for further study were rigorously cloned out at least three times by a limiting dilution method before being expanded for ascites production or scale-up by in vitro techniques.

Reverse and Competitive ELISA assays were used to establish the specificity and usefulness of the monoclonal antibodies produced.

EXAMPLE 14

Assays

For the forward ELISA assays, Costar EIA plates were coated with 50 $\mu$L/well affinity purified rabbit anti-mouse IgG+IgM+IgA antisera (1.0 mg/ml stock diluted 1:100 in phosphate buffered saline (PBS)) and incubated at 37° C. for one hour. The plates were blocked by adding 300 $\mu$L/well of 1% normal sheep sera (NSS) in PBS and incubated as before. The liquid was then shaken from the plate, and 50 μL/well of spent media antibody was then added and incubated as in the previous step. The plates were then washed three times using the ELISA wash buffer (PBS plus 0.05% Tween 20, pH 7.2). In the reverse ELISA assay, 50 μL/well of synthetic C9 amino acidanalog-G6PDH conjugate (diluted 1:400 in PBS) was added. When screening by the Competitive ELISA assay, 50 μL/well of the synthetic C9 amino acid analog of Example 10 in 100 μg/mL of diluted enzyme conjugate was added. The plates were incubated for 30 minutes at 37° C., and washed three times. 75 μL/well of substrate (0.1275M Tris, 0.04M NAD, 0.066M G-6-P, 0.3 mg/mL INT [4-iodo 2,4-nitrophenyl 3-5-phenoltetrazolium chloride], and 0.6 IU/mL diaphorase with 1% NSS) was then added and incubated until adequate color developed. The absorbance of each well at 492 nm was read.

The panel of monoclonal antibodies selected in the ELISA assays was next examined for performance in an EMIT ® assay protocol. The EMIT assay protocol is described in U.S. Pat. No. 3,517,837. Stock calibrators of synthetic C9 amino acid analog containing 0, 5, and 20 μg/mL were diluted 1:5 in assay buffer and 50 μL of the diluted calibrator and various amounts of spent media antibody were combined and diluted to 250 uL with assay buffer. NAD and glucose-6-phosphate substrate and the enzyme conjugate were added, 50 μL each +250 μL assay buffer and the change in absorbence at 340 nm was measured over a 30 second period. The results for antibody designated Cy XV 8C4 are summarized in (Table 1).

TABLE 1

Performance of Cy XV 8C4 Spent Media Antibody in EMIT* Assay

| Antibody (μL) | Absorbence at 340 mm | | |
|---|---|---|---|
| | 0 μg/ml | 15 μg/ml | 20 μg/ml |
| 250 | 227 | 244 | 472 |
| 150 | 358 | 367 | 590 |
| 50 | 633 | 651 | 744 |
| | 783 | | |

The invention provides for the preparation of reagents useful in an assay for the determination of cyclosporin, wherein the preparation of the reagents can be carried out in a relatively short number of steps. The reagents can be prepared in an optically active state and enantiomerically pure with good yields.

Although the foregoing invention has been described in some detail by way of illustration and example for the purpose of clarity and understanding, it will be obvious that certain changes and modifications may be practiced within the scope of the appended claims.

What is claimed is:

1. A compound of the formula:

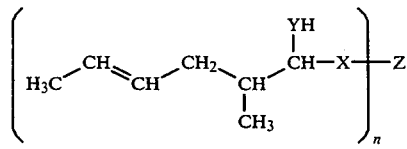

wherein:
X is a linking group of 0–65 atoms not counting hydrogen, said atoms being independently selected from the group consisting of O, S, P, N, Si, C and halogen, Z is a luminescent label, a group of molecular weight greater than 5000 which is an immunogenic carrier or an enzyme, or a ligand, or a hapten;

Y is oxygen or sulfur; and n is a number from 1 up to the molecular weight of Z divided by 1000;

and including the optically active isomers thereof.

2. The compound of claim 1 wherein Y is oxygen.

3. The compound of claim 2 wherein X is —CH₂OA and A is a linking group of 0–63 atoms not counting hydrogen and is bonded to —CH₂O through a carbon atom and is bonded to Z.

4. The compound of claim 3 wherein A contains a nonoxocarbonyl bonded to Z.

5. The compound of claim 3 wherein said carbon atom is bonded to W as C=W and W is O, S or NR and R is H or lower alkyl.

6. The compound of claim 5 wherein said C=W is bonded to NRX' and X' is a linking group having from 0 to 60 atoms not counting hydrogen.

7. The compound of claim 1 wherein Z comprises a poly(amino acid).

8. The compound of claim 1 wherein Z is an enzyme.

9. The compound of claim 1 wherein Z is glucose-6-phosphate dehydrogenase.

10. The compound of claim 9 wherein n is a number from 4 to 10.

11. The compound of claim 1 wherein Z is an immunogenic carrier selected from the group consisting of immunogenic poly(amino acids), lipopolysaccharides, and particles which are 0.01 microns to 100 microns in diameter.

12. The compound of claim 1 wherein Z is a luminescent label selected from the group consisting of fluorogenic substrates, fluorescers, chemiluminescers, and fluorescent particles.

13. A compound of the formula:

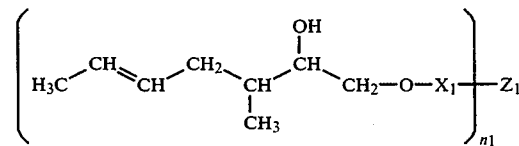

wherein:
X₁ is a linking group of 0 to 35 atoms not counting hydrogen, which atoms are each independently selected from the group consisting of carbon, oxygen, nitrogen, and sulfur, wherein X₁ is bonded to O through a carbon atom;

Z₁ is a poly(amino acid) of molecular weight greater than 5000 which is an antigen or an enzyme;

n₁ is a number from 1 up to the molecular weight of Z₁ divided by 1000;

including the optically active isomers thereof.

14. The compound of claim 13 wherein X₁ includes non-oxocarbonyl group.

15. The compound of claim 13 wherein X₁ comprises a carbamate functional group.

16. The compound of claim 13 wherein X₁ is a linking group of from 2 to 10 atoms not counting hydrogen.

17. The compound of claim 13 wherein Z₁ is a poly(amino acid) which is an antigen.

18. The compound of claim 13 wherein $Z_1$ is selected from the group consisting of an albumin and a gamma globulin.

19. The compound of claim 13 wherein $Z_1$ is an enzyme.

20. The compound of claim 13 wherein $Z_1$ is glucose-6-phosphate dehydrogenase.

21. The compound of claim 13 wherein $n_1$ is a number from 4 to 12.

22. The compound of claim 13 which has an isomeric configuration of (2R, 3R).

23. A compound of the formula:

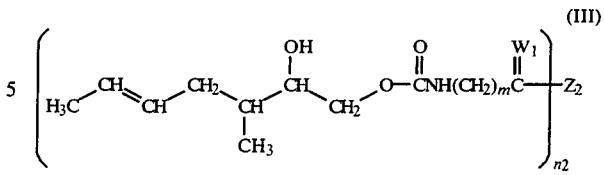

wherein:
$W_1$ is O, S, or NH;
m is 0 to 10;
$Z_2$ is a poly(amino acid) of molecular weight greater than 5000 which is an antigen or an enzyme;
$n_2$ is a number from 1 up to the molecular weight of $Z_2$ divided by 1000;
including the optical isomers thereof, 24. The compound of claim 23 wherein $W_1$ is 0.
25. The compound of claim 23 wherein m is 1 to 5.
26. The compound of claim 23 wherein $n_2$ is 4 to 12.
27. The compound of claim 23 wherein $Z_2$ is glucose-6-phosphate dehydrogenase.
28. The compound of claim 23 wherein $Z_2$ is an immunoglobulin.
29. The compound of claim 23 which has an isomeric configuration of (2R, 3R).

* * * * *